United States Patent [19]

Solanki

[11] Patent Number: 5,425,935
[45] Date of Patent: Jun. 20, 1995

[54] IMAGING OF INFECTIONS

[75] Inventor: Kishor K. Solanki, London, England

[73] Assignee: British Technology Group Limited, London, England

[21] Appl. No.: 50,092

[22] PCT Filed: Aug. 21, 1992

[86] PCT No.: PCT/GB92/01548

§ 371 Date: May 12, 1993

§ 102(e) Date: May 12, 1993

[87] PCT Pub. No.: WO93/03772

PCT Pub. Date: Mar. 4, 1993

[30] Foreign Application Priority Data

Aug. 23, 1991 [GB] United Kingdom ............... 9118183

[51] Int. Cl.$^6$ ..................... A61K 51/04; C07F 13/00
[52] U.S. Cl. .................... 424/1.65; 534/10; 534/14
[58] Field of Search ............. 424/1.1, 1.65; 534/10, 534/14; 544/255, 363

[56] References Cited

U.S. PATENT DOCUMENTS

| Re. 31,463 | 12/1983 | Loberg et al. | 424/1.1 |
|---|---|---|---|
| 5,093,105 | 3/1992 | Flanagan et al. | 424/1.1 |
| 5,153,203 | 10/1992 | Yatsunami et al. | 514/312 |
| 5,233,091 | 8/1993 | McGuirk | 546/431 |
| 5,245,026 | 9/1993 | Johnson et al. | 540/3 |
| 5,245,037 | 9/1993 | Kuramoto et al. | 546/156 |
| 5,262,417 | 11/1993 | Gammill et al. | 514/254 |
| 5,300,644 | 4/1994 | Hermecz et al. | 544/363 |

FOREIGN PATENT DOCUMENTS

| 0017355 | 10/1980 | European Pat. Off. . |
| 2197609 | 3/1974 | France . |
| 2281134 | 3/1976 | France . |
| 9109525 | 4/1991 | WIPO ............. A01N 43/00 |

OTHER PUBLICATIONS

Solomons, Organic Chemistry (4th Ed.), 1988, pp. 689–690.
H. M. Siefert et al "Pharmacokinetics of ciprofloxacin . . ." Abstract #12256h, Chemical Abstracts, vol. 106 No. 3, 13 Jan. 1987 (Columbus, Ohio, USA) p. 12.
T. Fujii et al "Distribution of (14C)AT-2266 . . . " #103538q, Chemical Abstracts, vol. 101 No. 13, 24 Sep. 1984 (Columbus, Ohio, USA), p. 13.
D. T. W. Chu et al "Structure-activity relationships . . . " Anticmicrobial Agents & Chemotherapy, vol. 33 No. 2, Feb. 1989 (Washington, D.C., USA) pp. 131–135.
G. Hoffken et al "Reduced enteral absorption . . . " European Jour. of Clin. Microbiology, vol. 4 No. 3, Jun. 1985 (Wiesbaden, DE), p. 345.

Primary Examiner—Gary Geist
Assistant Examiner—Lara E. Chapman
Attorney, Agent, or Firm—Nixon & Vanderhye

[57] ABSTRACT

A 4-quinolone antibiotic compound is used in gamma ray scintigraphy diagnostic imaging of a patient with a metallic radionuclide so as to locate focal infection.

12 Claims, 1 Drawing Sheet

IMAGING OF INFECTIONS

This invention relates to imaging and is particularly concerned with diagnostic imaging of infections with metallic radionuclides.

BACKGROUND OF THE INVENTION

The detection and identification of sites of bacterial infection, for example in a post-operative patient, has long been problematic. Thus the methods currently available for such diagnosis, such as scintigraphic scanning using radionuclides (e.g. Tc-99m and Ga-67) and radiolabelled Antibodies, are not specific in that they do not provide a means of distinguishing between infection foci and centres of inflammation. A specific method is available involving the In-111 oxime labelling of removed and purified white blood cells which are then reintroduced to the patient. Such a method is time-consuming and requires skilled manipulation in order to obtain a satisfactory result. It is important to differentiate between the two conditions, because there is bacterial involvement in infection, whereas inflammation, while sometimes following on from infection, is often attributable to mechanical damage. Thus the follow-up treatment differs for infection and inflammation and may be critical.

DESCRIPTION OF THE INVENTION

The present invention provides an entirely new solution to this problem in that it makes use of radionuclide-labelled antibiotics to specifically target sites of bacterial infection as opposed to inflammation and thus give a means of early identification of infection. Antibiotics are by no means the obvious candidate for use in radionuclide imaging. They are usually semi-synthetic in structure (for example, the penicillins) and do not lend themselves to complex formation with metals. They can cause the build up of resistance and sensitisation in the body. Furthermore, they are designed with a view to attaining therapeutic concentrations in most tissues of the body, rather than with a view to giving uptake purely at the sites of infection. It is not necessarily apparent that they are capable of giving a good target to background ratio.

According to the present invention, there is provided, for use in gamma ray scintigraphy diagnostic Imaging of a patient with a metallic radionuclide, a 4-quinolone antibiotic compound or a pharmacologically acceptable salt thereof.

The 4-quinolone antibiotics are a known class of antibacterial agents and those antibiotics-of this type which have already been recognised are reviewed by Chu et al., Antimicrobial Agents and Chemotherapy, 33, No. 2, 1989, 131–135. Thus the term "4-quinolone antibiotic" is intended to include structures containing the quinolone, naphthyridine and benzoxazine ring systems. Preferred quinolones are those bearing a 3-carboxy substituent, and preferably also a halogen substitutent at the 6-position, especially fluorine.

A preferred subgroup of 4-quinolone antibiotics are those having formula I:

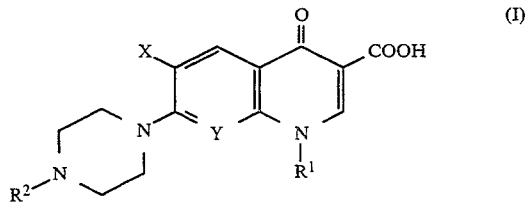

in which $R^1$ is a cyclic or acylic hydrocarbyl group which may be substituted, $R^2$ is hydrogen or an alkyl group, X represents a halogen atom, and Y is a nitrogen atom or a group $=CR^3$ where $R^3$ is hydrogen or an alkyl group, or $R^1$ and $R^3$, together with the ring carbon and nitrogen atoms to which they are attached, form a carbocyclic or heterocyclic ring, which may be substituted, or an optically active isomer of such a compound or a pharmaceutically acceptable salt of such a compound.

The halogen atom is preferably-fluorine.

One preferred example of a suitable antibiotic of formula I is that known as ciprofloxacin, which is a compound of formula I in which $R^1$ is cyclopropyl, Y is $=CH_2$, X is fluorine and $R^2$ is hydrogen. Further preferred examples are the compound of formula I in which Y is $CR^3$ and $R^1$ and $R^3$ together with the C and N atoms to which they are attached form a 2-methyl morpholino ring, X is fluorine and $R^2$ is methyl (known as ofloxacin) or the compound of formula I in which $R^1$ is ethyl, X is fluorine, Y is $=CH_2$ and $R^2$ is hydrogen (known as norfloxacin).

These quinolone antibiotics are purely synthetic antibiotics with a broad spectrum of antibacterial activity and little tendency to develop bacterial resistance. The primary mechanism of action of an antibiotic such as ciprofloxacin is considered to be inhibition of bacterial DNA gyrase, an enzyme vital in DNA replication.

It has previously been reported by Höffken et al., (Eur. J. Clin. Microb., 1985, 4 No: 3, p 345) and Smith et al., (Abstracts of the 6th Mediterranean Congress of Chemotherapy, 1988, Abstract No. 374, p 167) and, more recently, by Kara et al., Br. J. Clin. Pharmac., 1991, 31, 257–261 that the 4-quinolone antibacterials interact with certain multivalent metal ions such as magnesium and aluminium. These authors therefore concluded that care should be exercised in the administration of antacids together with these antibiotics in view of the reduction in bioavailability of the drug observed. This was viewed as a potential disadvantage of this type of antibiotic.

In contrast, in the present invention, the ability of the quinolone antibiotics to interact with certain metals is recognised as an advantage. Thus it has surprisingly been found that radionuclides such as technetium-99m will interact with compounds of formula I to give a complex which is still taken up by bacteria. Furthermore, it was found that the take up was considerably greater than for the known complex of Tc-99m with methylenediphosphonate (MDP) conventionally used in scintographic scanning, and used as a control.

The intended radionuclide for imaging is preferably Tc-99m, which is a known pharmaceutically acceptable radionuclide which is a pure gamma emitter with a short half life, making it well suited to use in in vivo imaging. Tc-99m Is routinely obtained from a "generator system" In the form of pertechnetate (TcO4—) which requires reduction to render it suitable for complexation. However, other metallic radionuclides not requiring reduction are also contemplated for use in accordance with the invention, for example Ga-67, In-111, or In-113m.

When using a radionuclide requiring reduction, the means are required capable of providing the radionuclide in a lower oxidation state and are selected dependent on the nature of the radionuclide. Generally a suitable chemical reducing agent is employed. For Tc-99m, a preferred reducing agent is a non metal reducing agent such as formamidine sulphonic acid (FSA) but other reducing agents are contemplated, such as the stannous halides (e.g. stannous chloride), stannous tartrate and other stannous compounds, metallic tin, a mixture of ascorbic acid with ferric chloride, concentrated hydrochloric acid-sodium borohydride, sodium dithionite or ferrous sulphate. Alternatively, means capable of reducing the radionuclide may be established by electrolysis. A further alternative is the provision of the desired complex by ligand exchange with a labile complex in which Tc exists in a desirable low oxidation state.

Therefore, according to a further aspect of the invention, there is provided a kit, intended for use in gamma ray scintigraphy diagnostic imaging of a patient with a metallic radionuclide, the Kit comprising a 4-quinolone antibiotic compound or a pharmacologically acceptable salt thereof, together with means capable of providing in a lower oxidation state the metallic radionuclide to be used in the imaging.

The invention also comprises, in combination, a metallic radionuclide such as Tc-99m, together with a kit as described above. The kit, with or without the Tc-99m, may conveniently be supplied in a form suitable for intravenous injection. In such a case a carrier vehicle such as saline is used for the antibiotic and any reductant. A convenient form of application is to supply a lyophilised admixture of reductant and antibiotic to which pertechnetate in saline is added to form an injectable solution.

Preferably the kit of the invention comprises a single dosage, for example 1 to 100 mg of the antibiotic (i.e. less than would be required for clinical use) together with up to an equivalent amount of reductant. Such amounts are suitably intended for use with a dose of for example 200 MBq to 800 MBq of Tc-99m as radionuclide. Any diluent or carrier is present so as to give a dose volume for injection suitably of up to 5 ml.

It will be appreciated that salts of the 4-quinolones can be employed, for example acid salts, such as hydrochlorides, or amine salts. Where the compounds exhibit chirality, optically active forms of the compounds may be employed selectively to give an enhanced imaging effect.

The present invention also includes the use of a kit as defined above, together with the metallic radionuclide in the gamma ray scintigraphy diagnostic imaging of a patient with the intention of locating focal infection. In addition, the invention includes the use of a compound of formula I, or a salt thereof, in the preparation of a Kit intended for use in the gamma ray scintigraphy diagnostic imaging of a patient with a metallic radionuclide so as to locate focal infections.

The invention further includes a method of locating focal infection in a patient comprising gamma ray scintigraphy diagnostic imaging of a patient to whom has been administered a metallic radionuclide labelled 4-quinolone antibiotic compound or a pharmacologically acceptable salt thereof.

BRIEF DESCRIPTION OF THE DRAWINGS

The invention will now be further described with references to the following

EXAMPLES

Figure 1:
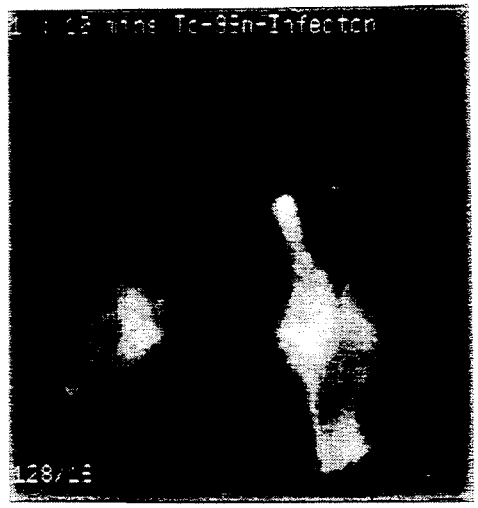
FIG. 1 shows the Tc-99m-ciprofloxacin image at 10 minutes after injection into a human hand.

The invention is further illustrated by the following examples.

Example 1. Preparation of Tc-99m-ciprofloxacin complex

Ciprofloxacin was obtained from Bayer Pharmaceuticals in the form of an intravenous preparation containing 2 mg (as lactate)/ml. This preparation was then aliquoted (0.5 mls) into sterile nitrogen vials (Amersham) using BD-insulin syringes (micro-fine IV). (The insulin syringes were used as they were less than 25G×⅝ (16 mm 5/10) in metal needle size. Therefore this minimises contamination from the free metal ions from the needle). These aliquots were kept refrigerated and away from light until required.

Formamidine sulphonic acid (FSA) was obtained from Sigma Chemical Company (F5877). On the day of preparation freshly prepared solution containing 1 mg/ml was made using 100 ml water for injection (Phoenix Pharmaceuticals). 100 µg was then transferred to the nitrogen vial containing the ciprofloxacin using a fine diabetic syringe.

High specific activity (>1000MBq/ml) Tc99m pertechnetate was obtained from an Amertec II generator (Amersham). Best results were obtained with pertechnetate from a generator which had been eluated in the past 24 hours.

500MBq of pertechnetate were aseptically introduced into the vial. The reaction mixture was boiled for 10 minutes after the radionuclide addition. After filtering through a Sephadex DEAE A25 column the resulting complex was assayed as having a radiochemical purity of 98%±3%. The assay was carried out using a two stage chromatography system, employing, in the first stage, instant thin layer chromatography silica gel paper (ITLC-SG, Gelman) run in acetone. Free pertechnetate was located with the solvent front. In the second stage, there was employed plastics-backed silica gel (60) plates (Merck) with a solvent of methanol: normal saline: acetic acid 45:55:1. The Tc-99m ciprofloxacin was located as a single peak at Rf of 0.8.

Example 2. Preparation of Tc-99m-ciprofloxacin complex

A Tc-99m-ciprofloxacin complex suitable for clinical usage was prepared by the following alternative method to that given in Example 1, and designed with a view to routine clinical use.

Formamidine sulphonic acid (FSA) (obtained from Sigma Chemical Company) was freshly prepared (1 mg/ml) and the pH adjusted to 7.8 to 8.0. The solution was aliquoted into sterile nitrogen vials and freeze dried. The lyophilised vials were stored in boxes in a refrigerator.

When the Tc-99m-ciprofloxacin was required, ciprofloxacin (2 mg/ml) (obtained from Bayer Pharmaceuticals) was adjusted to pH 7.0 to 7.2. The resulting solution (1 mg) was added to a freeze dried kit of FSA using a BD-insulin syringe. This was immediately followed by addition of Tc-99m-pertechnetate (500MBq) from a solution of eluate from a generator containing at least 1000MBq/ml. The mixture was shaken, boiled for 10 minutes and then cooled.

To assay the radiochemical purity of the solution, a two stage chromatography system was used. An instant thin layer chromatography (ITLC-SG, Gelman) run in 95% acetone or methyl ethyl ketone, enabled the determination of free pertechnetate, which was located at the solvent front. The second system used Whatman 3M paper run in 1M hydrochloric acid. With that system the Tc-99m-ciprofloxacin moved with the solvent front. The percentage activity remaining at the base gave an estimated level of reduced hydrolysed complex. The mean percentage of radiochemical purity was calculated at 85 to 90%.

If further purification is felt to be essential, the solution may be passed through a Sephadex DEAE A25 column attached to a terminal filter (2.5 cm with pore size 0.22 $\mu$).

Example 3. Take Up of Tc-99m-ciprofloxacin by bacteria

Bacterial broths containing Staphylococcus aureus (SA), Pseudomonas aboubinoba (PA) and Escherichia coli (EC) were obtained from a hospital microbiology department. Bacterial samples (1 ml, containing $10^9$ counts) were in each case incubated with 0.5 mi Tc-99m-ciprofloxacin (CIP) prepared as described in Example 1 but not further purified. Comparison experiments were carried out on 1 ml bacterial samples using 0.5 mi of Tc-99m-methylenediphosphonate (MDP). After time periods of 2, 4 and 21 hours incubation, 0.1 $\mu$l samples were placed in a Gelman acrodisc filter (0.2 $\mu$ size) and washed with normal saline (1 ml). The results are given in Table 1 below in the form of percentage radionuclide retained in the microorganisms.

TABLE 1

|    | Tc-99 m CIP |       |        | Tc-99 m MDP |
|----|-------------|-------|--------|-------------|
|    | 2 hr.       | 4 hr. | 21 hr. | 21 hr.      |
| SA | 17.24       | 14.63 | 15.08  | 0.67        |
| PA | 24.14       | 16.67 | 21.32  | 2.43        |
| EC | 15.78       | 11.72 | 12.90  | 1.02        |

Example 4.

A further sample of Tc-99m-CIP complex was obtained as generally described in Example 1. Samples of Tc-99m complexed ofloxacin (obtained in powder form from Hoechst) and norfloxacin (obtained in powder form from Merck Sharpe & Dohme) were obtained as described for ciprofloxacin. Prior to purification, it was determined that the extent of complexation percent was as follows:

| ciprofloxacin | 51.7 |
| ofloxacin     | 88.5 |
| norfloxacin   | 76.5 |

Example 5

The complexes prepared as described in Example 4 were further purified by boiling (15 minutes) and passage through a Sephadex purification column (1 inch Sephadex DEAE A25 mini column). The purified complexes were tested as described in Example 3 In order to demonstrate in-vitro bacterial uptake. The results are shown in Table 2 below after 4 hours' incubation as percent radionuclide retained in the microorganism.

TABLE 2

|               | EC    | SA    | PA    |
|---------------|-------|-------|-------|
| ciprofloxacin | 43.89 | 58.47 | 50.20 |
| ofloxacin     | 77.95 | 76.94 | 79.39 |
| norfloxacin   | 48.28 | 37.86 | 44.53 |

Example 6.

Tc-99m CIP (in an amount of between 50 to 70MBq) was injected into a New Zealand white rabbit exhibiting an infected lower limb. The images were obtained using a IGE gamma camera fitted with a medium energy collimator, showing uptake in the infected limb. The data was collected into a Nodecrest system 3. The animal was fastened flat onto the gamma camera to reduce movement artifacts. The biodistribution of the labelled Tc99m ciprofloxacin was similar to that documented for unlabelled ciproflaxacin, i.e. generally diffuse uptake throughout the body with main uptake in the kidneys and the liver, together with rapid renal clearance (>20% dose in 4 hours).

Example 7.

Tc-99m CIP labelling of a patient in vivo was carried out using initially prepared sterile nitrogen vials containing ciprofloxacin and formamidine sulphonic acid in accordance with the following instructions. It is to be noted that the prepared labelled material is of a pharmaceutically injectable grade, since all ingredients are sterile, particle free and isotonic, and the preparation is undertaken under aseptic conditions as defined by BS 5295.

1. Working under aseptic conditions undertake the following procedure.

2. Switch on water-bath ready for the boiling step in the procedure.

3. Place a vial of ingredient in a convenient lead shield.

4. Aseptically introduce into the vial, 500MBq of sterile and pyrogen-free Tc99m-pertechnetate (high specific activity, preferably <0.5 ml volume) using an orange needle and 1 ml syringe provided.

5. Mix and place vertically (preferably) in boiling water-bath for at least 15 minutes. Keep the water-bath covered.

6. After 15 minutes cool under a cold water tap or in icy cold water container for a few minutes.

7. Prepare Sephadex column by removing metal tab and disinfecting the ends.

8. Place Sephadex column vertically in the sterilin plastic container with the rubber septum at the top. There is no need to attach a needle to the base of the column.

9. Using a ml syringe and orange needle draw up the entire content from the boiled vial.

10. Transfer the content to the top of the Sephadex column.

11. Using a 5 ml syringe and an orange needle draw up 1 ml of sodium chloride 0.9% injection (saline) from the provided ampoule. Add this saline to the vial to wash the vial.

12. Transfer the wash onto the top of the Sephadex column.

13. Draw up the rest of the saline (4 mls) and pass it through the Sephadex column and allow the filtrate to collect in the sterilin plastic container.

14. After the final drop has passed through the column measure total activity collected, total activity on the Sephadex column and amount still remaining in the original vial.

15. Draw up activity in 5 ml syringe and attach a blue needle for injection.

16. Inject at least 100MBq of labelled product to each patient. 17. Scan patient with images at 1 hour, 2 hours and 4 hours. If necessary scan at 22 or 24 hours.

The results for a normal volunteer (in which localisation of infection was not expected) were as described below and showed fast clearing of the radioactivity.

The radiopharmaceutical showed immediate uptake into the liver, the spleen and the kidney consistent with high blood flow to those organs. The other areas showed diffused uptake typical of an antibiotic, but surprising in this instance, as this is a complexed radiopharmaceutical and not just the original antibiotic (which is not radioactive and therefore cannot be seen on the scan).

The ciprofloxacin:Tc99m could be a 3:1 complex or a bidentate structure : therefore its biological behaviour both pharmacologically and pharmacokinetically can not be extrapolated from the parent antibiotic. It appears that the proximity of the carboxyl and the keto groups on the ciprofloxacin molecule account for a good stable complex with the Tc99m. There appeared to be no uptake in the stomach, salivary glands or the thyroid, thus reflecting good in vivo stability of the complex. The generalised diffused uptake faded with time and appeared faint in four hour images. These four hour scans still showed no other specific organ uptake. There was a noticable absence of radiopharmaceutical complex in the thyroid, stomach or the salivary glands in images at four hours and even 18 hours, again reflecting in vivo stability of the Tc99m ciprofloxacin complex.

The liver and Kidney activity faded with time, reflecting non-specific uptake and excretion. The bowel remained clear, which could be important for focusing on abdominal abscesses (a major clinical problem) and differentiating inflammatory bowel disease from infective bowel disease, which is not currently possible.

Analysis of the renal clearance data suggested a value of 230 ml/min for Tc99m:ciprofloxacin complex, which appeared to be faster than just the glomeruli filtration rate and therefore suggestive of some active tubular excretion. It is known that parent ciprofloxacin is actively excreted from the renal tubules. The tubular excretion is a substrate specific process : therefore the Tc99m:ciprofloxacin complex still appears to exhibit certain substrate features common to the parent antibiotic. This is useful, as the active tubular excretion is a key to obtaining better contrast of the infection foci.

Example 8.

Figure 2:
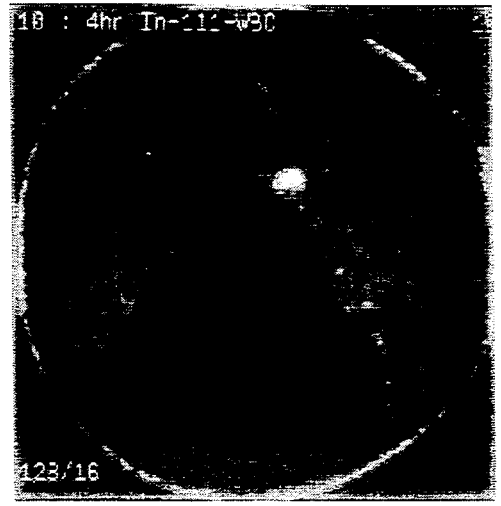
FIG. 2 shows the In-111-WBC image at four hours after injection.
Figure 3:
FIG. 3 shows the Tc-99m-MDP bone scan image three hours after injection.

The following clinical trial further illustrates the invention with reference to FIGS. 1, 2 and 3.

A 51 year old man developed an apical subungual infection of his right 2nd finger, which led to gangrenous changes around the distal end. This was treated surgically and the distal phalanx was removed. He was treated with antibiotics : however the surgical wound continued to be infected. At this stage scans were carried out with Tc-99m-ciprofloxacin (prepared as described in Example 1), In-Ill-white blood cells (WBC) and Tc-99m-MDP. The results are shown in FIGS. 1, 2 and 3 respectively.

FIG. 1 shows the Tc-99m-ciprofloxacin image at 10 minutes post injection. The image of the hands shows an increased tracer uptake around the distal end of the right 2nd finger corresponding to the site of infection. Slightly prominent activity was also observed in the rest of the finger which extended into the thenar region due to increased vascularity. This distribution pattern of the tracer persisted up to 4 hour post injection.

FIG. 2 shows the In-111-WBC image at 4 hours post injection. The image shows an area of increased tracer uptake at the distal end of the right 2nd finger corresponding to the site of infection.

FIG. 3 shows the Tc-99m-MDP bone scan image at 3 hours post injection. The image shows tracer uptake in the middle phalanx of the right 2nd finger. In addition, increased tracer uptake was also observed in the left and right distal interphalangeal joint of the 3rd finger, right 2nd metacarpophalangeal joint and right wrist joint due to acute arthritic changes.

It is to be noted that the Tc-99m-ciprofloxacin allowed demonstration of the infected finger within 10 minutes of injection. This was confirmed by a conventional In-111-NBC scan at 4 hours. The Tc-99m-MDP bone scan was non-specific for the infection.

I claim:

1. A metallic radionuclide labelled 4-quinolone antibiotic compound in which the antibiotic compound is a 4-quinolone antibiotic of formula I:

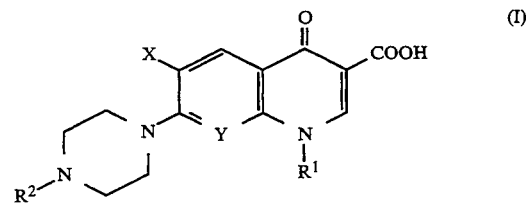

in which $R^1$ is a cyclopropyl, ethyl, or 4-fluorophenyl group, $R^2$ is hydrogen or a methyl group, X represents a halogen atom, and Y is a nitrogen atom or a group $>CR^3$ where $R^3$ is $H_2$ or a methyl group, or $R^1$ and $R^3$, together with the ring carbon and nitrogen atoms to which they are attached, form a 2-methyl morpholino ring, or an optically active isomer of such a compound or a pharmaceutically acceptable salt of such a compound.

2. A 4-quinolone antibiotic compound or a pharmacologically acceptable salt thereof according to claim 1 labelled with a radionuclide selected from the group consisting of Tc-99m, Ga-67, In-111 and In-113 m.

3. A metallic radionuclide labelled 4-quinolone antibiotic compound or salt thereof according to claim 1 where X in formula I is fluorine.

4. A metallic radionuclide labelled 4-quinolone antibiotic compound or salt thereof according to claim 3 wherein $R^1$ is cyclopropyl, Y is $>CH_2$, and $R^2$ is hydrogen.

5. A metallic radionuclide labelled 4-quinolone antibiotic compound or salt thereof according to claim 3 wherein Y is $>CR^3$ and $R^1$ and $R^3$ together with the C and N atoms to which they are attached form a 2-methyl morpholino ring and $R^2$ is methyl.

6. A metallic radionuclide labelled 4-quinolone antibiotic compound or salt thereof according to claim 3 wherein $R^1$ in formula I is ethyl, Y is $>CH_2$ and $R^2$ is hydrogen.

7. A method of locating focal infections in a patient comprising subjecting a patient to gamma ray scintigraphy diagnostic imaging to whom has been administered a metallic radionuclide labelled 4-quinolone antibiotic compound or a pharmacologically acceptable salt thereof according to claim 1.

8. A kit suitable for use in gamma ray scintigraphy diagnostic imaging of a patient with a metallic radionuclide, said kit comprising:

a 4-quinolone antibiotic compound or a pharmacologically acceptable salt thereof as defined in claim 1; and means for producing in a lower oxidation state the metallic radionuclide to be used in the imaging.

9. A kit according to claim 8 wherein said means comprises a chemical reducing agent.

10. A kit according to claim 8 wherein the components are in a form suitable for intravenous injection.

11. A kit according to claim 8 further comprising the metallic radionuclide to be used in the imaging.

12. A kit according to claim 11 wherein the radionuclide is technetium-99m.

* * * * *